US008889143B2

(12) United States Patent
Humphreys et al.

(10) Patent No.: US 8,889,143 B2
(45) Date of Patent: *Nov. 18, 2014

(54) Ii-KEY/HER-2/NEU HYBRID CANCER VACCINE

(75) Inventors: Robert Humphreys, Acton, MA (US); Minzhen Xu, Northborough, MA (US)

(73) Assignee: Antigen Express, Inc., Worcester, MA (US)

( * ) Notice: Subject to any disclaimer, the term of this patent is extended or adjusted under 35 U.S.C. 154(b) by 937 days.

This patent is subject to a terminal disclaimer.

(21) Appl. No.: 12/635,656

(22) Filed: Dec. 10, 2009

(65) Prior Publication Data

US 2010/0150953 A1    Jun. 17, 2010

Related U.S. Application Data

(63) Continuation-in-part of application No. 12/002,083, filed on Dec. 13, 2007, now Pat. No. 7,935,350.

(60) Provisional application No. 60/874,842, filed on Dec. 14, 2006.

(51) Int. Cl.
*A61K 38/04* (2006.01)
*A61K 39/00* (2006.01)

(52) U.S. Cl.
CPC ... *A61K 39/0011* (2013.01); *A61K 2039/55522* (2013.01); *A61K 2039/55516* (2013.01)
USPC .................. 424/192.1; 424/184.1; 424/185.1; 424/193.1

(58) Field of Classification Search
USPC ...................... 424/184.1, 185.1, 192.1, 193.1
See application file for complete search history.

(56) References Cited

U.S. PATENT DOCUMENTS

| 5,726,023 | A | 3/1998 | Cheever et al. |
| 5,846,538 | A | 12/1998 | Cheever et al. |
| 2003/0235594 | A1 | 12/2003 | Humphreys et al. |
| 2006/0002947 | A1* | 1/2006 | Humphreys et al. ....... 424/185.1 |

OTHER PUBLICATIONS

Jin, H., et al., Vaccine, 22: 2925-2935, 2004.*
Liu, M. A., et al Human Gene Therapy, 17: 1051-1061, 2006.*
Renard, V., et al. The Journal of Immunology, 171: 1588-1595, 2003.*
Sotiriadou, N. N., et al. Cancer Immunology: Immunotherapy, in press (online Sep. 8, 2006).
Bertolino, P., and Rabourdin-Combe, C. Crit. Rev. Immunol. 16:359-379 (1996).
Bodmer, H., et al. Science 263:1284-1286 (1994).
Xu, M., et al. Mol. Immunol. 31:723-731 (1994).
Daibata, M., et al. Mol. Immunol. 31:255-260 (1994).
Reyes, V. E., et al. Ann. NY Acad. Sci. 730:338-341 (1994).
Bakke, O., and Dobberstein, B. Cell. 63:707-716 (1990).
Lamb, C.A., and Cresswell, P. J. Immunol. 148:3478-3482 (1992).
Blum, J. S., and Cresswell, P. Pro. Natl. Acad. Sci. USA 85:3975-3979 (1988).
Nguyen, Q. V., et al. Hum. Immunol. 24:153-163 (1989).
Shi, G.P. et al. J. Exp. Med. 191:1177-1186 (2000).
Riese, R. J., et al. Immunity 4:357-366 (1996).
Hiltbold, E. M., and Roche, P. A. Curr. Opin. Immunol. 14:30-35 (2002).
Riberdy, J. M., et al. Nature 360:474-477 (1992).
Gautam, A.M., et al. Proc. Natl. Acad. Sci. USA 92:335-339 (1995).
Romagnoli, P., and Germain, R. N. J. Exp. Med. 180:1107-1113 (1994).
Morris, P., et al. Nature 368:551-554 (1994).
Denzin, L. K., and Cresswell, P. Cell. 82:155-165 (1995).
Xu, M., et al. Arzneimittelforschung 49:791-799 (1999).
Adams, S., et al. Arzneimittelforschung 47:1069-1077 (1997).
Lu, S., et al. J. Immunol. 145:899-904 (1990).
Adams, S., and Humphreys, R. E. Eur. J. Immunol. 25:1693-1702 (1995).
Humphreys, R. E., et al. Vaccine 18:2693-2697 (2000).
Ghosh, P., et al. Nature 378:457-462 (1995).
Stevanovic, S., and Rammensee, H. G. Behring Inst. Mitt. 7-13 (1994).
Rammensee, H. G., et al. Immunogenetics 41:178-228 (1995).
Hakenberg, J., et al. Appl. Bioinformatics 2:155-158 (2003).
Knutson, K. L., et al., Clin. Cancer Res. 8:1014-1018 (2002).
Phan, G. Q., et al., J. Immunother 26:349-356 (2003).
Brinkman, J. A., et al. Expert Opin. Biol. Ther. 4:181-198 (2004).
Hersey, P., et al. Cancer Immunol. Immunother. 54:208-218 (2005).
Xu, M., et al. Scand. J. Immunol. 54:39-44 (2001).
Gillogly, M. E., et al. Cancer Immunol. Immunother. 53:490-496 (2004).
Kallinteris, N. L., et al. Vaccine 21:4128-4132 (2003).
Kallinteris, N. L., et al. Vaccine 23:2336-2338 (2006).
Kallinteris, N. L., et al. J. Immunother. 28:352-358 (2005).
Touloukian, C. E., et al. J. Immunol. 164:3535-3542 (2002).
Kallinteris, N. L., et al. Frontiers in Bioscience: 46-58 (2006).
Fleckenstein, B., et al. Semin. Immunol. 11:405-416 (1999).

(Continued)

*Primary Examiner* — Ram R Shukla
*Assistant Examiner* — Anne Holleran
(74) *Attorney, Agent, or Firm* — Pierce Atwood LLP; Kevin M. Farrell; David J. Wilson

(57) ABSTRACT

Provided are methods and compositions for treating cancer in humans, the cancer being characterized by expression of Her-2/neu. The methods involve vaccinating a patient with an Ii-Key/MHC class II hybrid construct and thereby stimulating an immune response to the native Her-2/neu protein. The construct may be in the form of an Ii-Key hybrid peptide or a nucleic acid encoding an Ii-Key hybrid peptide. Methods are described wherein the cancer being treated is breast cancer. Also claimed is a pharmaceutical composition comprising an Ii-Key/MHC class II hybrid construct with and without an adjuvant. The adjuvant can include GM-CSF. The Ii-Key hybrid construct includes the LRMK (SEQ ID NO: 2) residues of Ii-Key protein and an MHC Class II epitope of a protein or portion thereof which is used in the vaccine or a DNA encoding the same hybrid peptide.

3 Claims, 13 Drawing Sheets

(56) References Cited

OTHER PUBLICATIONS

Joshi, R. V., et al. Biochemistry 39:3751-3762 (2000).
Wang, R. F. Immunol. Rev. 188:65-80 (2002).
Sette A., and Fikes, J. Curr. Opin. Immunol. 15:461-470 (2003).
Hanson, H. L., et al. J. Immunol. 172:4215-4224 (2004).
Wong, R., et al. Clin. Cancer. Res. 10:5004-5013 (2004).
Hung, K., et al. J. Exp. Med. 188:2357-2368 (1998).
Surman, D. R., et al. J. Immunol. 164:562-565 (2002).
Welsh, R. M., et al. Annu. Rev. Immunol. 22:711-743 (2004).
Knutson, K. L., and Disis, M. L. Cancer Immunol. Immunother. (2005).
Rocha B., and Tanchot, C. Curr. Opin. Immunol. 16:259-263 (2004).
Janssen, E. M., et al. Nature 434:88-93 (2005).
Dissanayake, S. K. et al. Cancer Res. 64:1867-1874 (2004).
Ossendorp, F., et al. J. Exp. Med. 187:693-702 (1998).
Dudley, M.E., et al. Science 298:850-854 (2002).
Robbins, P. F., et al. J. Immunol. 169:6036-6047 (2002).
Gao, F. G., et al. Cancer Res. 62:6438-6441 (2002).
Yu, P., et al. J. Exp. Med. 197:985-995 (2003).
Anthony, P. A., et al. J. Immunol. 174:2591-2601 (2005).
Mandic M., et al. J. Immunol. 174:1751-1759 (2005).
Lu, J. et al. J. Immunol. 172:4575-4582 (2004).
Slager, E. H., et al. J. Immunol. 172:5095-5102 (2004).
Delcayre, A., and Le Pecq, J. B. Opin. Mol. Ther. 8:31-38 (2006).
Sanders, M. T., et al. Immunol. Cell. Biol. 83:119-28 (2005).
Nagata, Y., et al. Pro. Natl. Acad. Sci. USA 99:10629-34 (2002).
Tobian, A. et al. J. Immunol. 172:5277-86 (2004).
Zimmerman, D. H., and Rosenthal, K. S. Front. Biosci. 10:790-798 (2005).
Franke, E. D., et al. Vaccine 17:1201-5 (1999).
Nagata, T., et al. Vaccine 20:105-14 (2001).

* cited by examiner

SEQUENCE LISTING

```
<160> NUMBER OF SEQ ID NOS: 5

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Leu Arg Met Lys Leu Pro Lys
1               5

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Leu Arg Met Lys
1

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Val Gly Ser Pro Tyr Val Ser Arg Leu Leu Gly Ile Cys Leu
```

```
1               5                   10                  15

<210> SEQ ID NO 4
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Leu Arg Met Lys Gly Val Gly Ser Pro Tyr Val Ser Arg Leu Leu Gly
1               5                   10                  15

Ile Cys Leu

<210> SEQ ID NO 5
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ava

<400> SEQUENCE: 5

Leu Arg Met Lys Xaa Tyr Val Asp Arg Phe Tyr Lys Thr Leu Arg Ala
1               5                   10                  15

Glu Gln
```

II-KEY/HER-2/NEU HYBRID CANCER VACCINE

BACKGROUND OF THE INVENTION

Breast cancer is the most common cancer in women. Most breast cancers are detected early and treated with multimodality therapy including surgery, chemotherapy and radiation therapy. Despite patients being rendered disease free with this intensive therapy, many women with high risk features will have recurrent disease. Over expression of the Her-2/neu protein is one such high risk feature.

The epithelial cell adhesion molecule, Her-2/neu is a member of the epidermal growth factor receptor family, normally expressed during fetal development. Amplification of the gene and over-expression of the protein product have been described in a number of epithelial tumors and are markers of high recurrence risk in breast cancer. Immunotherapy directed against Her-2/neu can control the growth of these tumors. The Her-2/neu protein is over-expressed in 30-40% of early stage breast cancer and that over-expression is associated with poor clinical outcome. Other cancers in which Her-2/neu is over-expressed include ovary, recto-colon, lung, prostate, stomach, pancreatic, and biliary cancer (Sotiriadou, N. N., et al. Cancer Immunology Immunotherapy, in press (online Sep. 8, 2006)).

The Her-2/neu protein is also a source of immunogenic peptides. Immunogenic peptides of Her-2/neu can stimulate cytotoxic T lymphocytes (CTL) to recognize and kill Her-2/neu expressing cancer cells in vitro. Some of the peptides (E75 and GP2) are being used in clinical trials as vaccines in patients with Her-2/neu+ breast cancers. Thus far, they have been shown to be safe in patients and effective in stimulating antigen specific immunity; more importantly, we have shown that the immunity conferred by E75 appears to have clinical benefit in preventing recurrence of breast cancer. Unfortunately, the immunity conferred by these peptide vaccines is not sustained. Helper peptides may be required to increase the efficiency of induction and establishment of long-term immunity.

Helper peptides for Her-2/neu have been described. The MHC Class II associated Ii protein normally blocks the processing of endogenous peptides, preventing attachment to MHC and antigen presentation. Suppression of the Ii protein in tumor cell lines and rat tumor models has been shown to induce tumor antigen presentation and enhance antigen specific tumor cell killing.

The Ii protein normally binds to MHC class II molecules in the endoplasmic reticulum at synthesis and protects the epitope-binding site on MHC class II molecules from binding to endogenously-derived epitopes in the endoplasmic reticulum, as normally occurs with MHC class I molecules [Bertolino, P. and Rabourdin-Combe, C., *Crit. Rev Immunol* 16:359-379 (1996); Bodmer, H., et al., *Science* 263:1284-1286 (1994)]. Another major function of the Ii protein is to enhance exogenous peptide charging to MHC class II molecules [Xu, M., et al., *Mol Immunol* 31:723-731 (1994); Daibata, M., et al., *Mol Immunol* 31:255-260 (1994); Reyes, V. E., et al., *Ann NY Acad Sci* 730:338-341 (1994)]. The MHC class II/Ii complex is transported to a post-Golgi, antigenic peptide-binding compartment after synthesis [Bakke, O. and Dobberstein B., *Cell* 63:707-716 (1990); Lamb, C. A. and Cresswell, P., *J Immunol* 148:3478-3482 (1992); Blum, J. S, and Cresswell, P., *Proc Natl Acad Sci USA* 85:3975-3979 (1988)]. In such compartments, the Ii is cleaved by proteases to allow charging by exogenously derived epitopes. After being charged with epitopes, the MHC class II/epitope complex travels to the cell surface for presentation to CD4+ Th cells [Nguyen, Q. V et al., *Hum Immunol* 24:153-163 (1989); Shi, G. P., et al., *J Exp Med* 191:1177-1186 (2000); Riese, R. J., et al., *Immunity* 4:357-366 (1996); Hiltbold, E. M. and Roche, P. A., *Curr Opin Immunol* 14:30-35 (2002)]. Two mechanisms have been proposed to explain the function of Ii in enhancing the charging of epitopes to MHC class II molecules. First, Ii is partially digested to leave only a small segment behind, termed CLIP, which is bound to the epitope-binding groove of the MHC class II molecule in a manner to keep the groove open [Riberdy, J. M., et al., *Nature* 360:474-477 (1992); Gautam, A. M., et al., *Proc Natl Acad Sci USA* 92:335-339 (1995); Romagnoli, P. and Germain, R. N., *J Exp Med* 180:1107-1113 (1994)]. HLA-DM then exchanges CLIP for an epitope [Morris, P., et al., *Nature* 368:551-554 (1994); Denzin, L. K. and Cresswell, P., *Cell* 82:155-165 (1995)]. Secondly, in a concerted manner, Ii is digested and released from MHC class II molecules as epitopes are being charged [Xu, M., et al., *Mol Immunol* 31:723-731 (1994); Daibata, M., et al., supra; Reyes, V. E., et al., *Ann NY Acad Sci* 730:338-341 (1994)].

An important function of the Ii protein is evident in a short sequence that binds to an allosteric site outside of the epitope-binding groove [Xu, M., et al., *Arzneimittelforschung* 49:791-799 (1999)]. The result of this interaction is the maintenance of the epitope-binding groove in a conformation that is the most suitable for MHC class II molecules to exchange an epitope. That Ii sequence has been termed the Ii-Key peptide. The segment of the Ii containing amino acids hIi(77-92) regulates tightness of closure of the antigenic epitope-binding groove of MHC class II molecules. This segment first raised interest due to it's having 6 positive side chains, no negative side chains, and 4 prolines, which together appeared to constitute a signal for a protease or "exchange-ase"; ostensibly to regulate cleavage and release of the Ii [Adams, S., et al., *Arzneimittelforschung* 47:1069-1077 (1997); Lu, S., et al., *J Immunol* 145:899-904 (1990)]. Further studies showed that mutations in this segment do, in fact, block the staged cleavage and release of Ii [Xu, M., et al., *Mol Immunol* 31:723-731 (1994); Daibata, M., et al., supra]. In light of these findings, we synthesized the fragment of the Ii containing amino acids hIi(77-92), referred to as "Ii-Key". An initial study illustrated that the activation of hen egg white lysozyme (HEL)-specific T cell hybridoma by an HEL epitope peptide was enhanced by Ii-Key peptides up to 50-fold [Adams, S., and Humphreys, R. E., *Eur J Immunol* 25:1693-1702 (1995)]. Enhanced activation was observed even when using paraformaldehyde-fixed Antigen Presenting Cells (APCs), in which normal intracellular processing was not possible. Studies to further identify the minimal active sequence of Ii-Key revealed a 'core' LRMKLPK (SEQ ID NO: 1) structure that had greater potency than the original 16-amino acid peptide [Adams, S., et al., supra]. The Ii 77-80 (LRMK (SEQ ID NO: 2)) segment retained at least 50% of the activity of LRMKLPK (SEQ ID NO: 1). For simplicity, we therefore designed later Ii-Key/MHC class II epitope hybrids with this shorter, four-amino-acid, Ii-Key moiety.

In contrast to cell culture studies, in vivo inoculation of mice with Ii-Key plus an antigenic peptide failed to enhance the activity of that antigenic peptide [unpublished observations]. This suggested that the Ii-Key needed to be co-localized with the antigenic epitope to enhance presentation. The Ii-Key moiety was linked covalently to the MHC class II epitope to ensure that individual MHC class II molecules on the APC are exposed simultaneously to both Ii-Key and epitope. A systematic series of Ii-Key MHC class II epitope hybrids were synthesized and tested in an in vitro T cell hybridoma stimulation assay [Humphreys, R. E., et al., *Vaccine* 18:2693-2697 (2000)]. For this series of hybrids, the Ii-Key core (LRMK (SEQ ID NO: 2)) was joined to an MHC class II-restricted epitope of pigeon cytochrome C (PGCC81-104). The spacers joining Ii-Key and PGCC81-104 were either a simple polymethylene (δ-aminovaleric acid; ava) linker or the natural sequence of the Ii extending from the C-terminus of LRMK (SEQ ID NO: 2). The design of Ii-Key hybrids was based on biochemical and X-ray crystallographic data indicating that the Ii-Key binding site lies outside of the antigenic peptide-binding groove of MHC class II molecules [Ghosh P, et al., *Nature* 378:457-462 (1995)]. Both the length of the Ii-Key derivative and linker composition were varied within the series. Hybrids having either type of bridge were effective. Some hybrids enhanced presentation of an antigenic epitope up to 250 times above the baseline stimulation observed using the free antigenic peptide [Humphreys, R. E. et al., supra].

The discovery of numerous clinically relevant peptide epitopes, both MHC class I- and II-restricted, has increased the motivation to develop effective peptide vaccines. From these data, consensus motifs for both MHC class I- and II-restricted epitopes have been proposed [Stevanovic, S, and Rammensee, H. G., *Behring Inst Mitt:* 7-13 (1994); Rammensee, H. G., et al., *Immunogenetics* 41:178-228 (1995); Hakenberg, J., et al., *Appl Bioinformatics* 2:155-158 (2003)]. While some peptides of potential clinical importance have been identified and specific immune responses have been observed in patients treated with those peptides, good therapeutic efficacy has not been observed [Knutson, K. L., et al., *Clin Cancer Res* 8:1014-1018 (2002); Phan, G. Q., et al., *J Immunother* 26:349-356 (2003); Brinkman, J. A., et al., *Expert Opin Biol Ther* 4:181-198 (2004); Hersey, P., et al., *Cancer Immunol Immunother* 54:208-218 (2005)]. The main obstacle appears to be the relatively low affinity of some MHC class II-restricted epitopes. There is a need for peptide vaccine potency to breakdown tolerance to tumor antigens.

A novel technology has been developed based on using a portion of the Ii protein to enhance MHC class II epitope charging and thus the efficiency of Th cell activation [Adams, S., and Humphreys, R. E., supra; Adams, S., et al., supra; Xu, M., et al., *Arzneimittelforschung* 49:791-799 (1999); Xu, M., et al., *Scand J Immunol* 54:39-44 (2001)]. This "Ii-Key" segment of the Ii protein significantly enhances MHC class II epitope presentation in a variety of settings and creates a practical method to enhance the efficacy of MHC class II peptide vaccines. The Ii-Key segment binds an allosteric site on MHC class II molecules to loosen their epitope-binding groove, allowing the epitope segment to directly charge MHC class II molecules present on the cell surface [Adams, S., et al., supra; Xu, M., et al., *Arzneimittelforschung* 49:791-799 (1999)]. In-Key hybrids are composed of the Ii-Key moiety linked to the N-terminus of an MHC class II epitope. This linkage can be of several forms, including a simple polymethylene bridge or the natural sequence of Ii extending from the C-terminus of LRMK (SEQ ID NO: 2) or natural amino acids (extending from the N-terminal of the MHC class II epitope) of the protein from which the MHC class II epitope peptide was obtained.

Ii-Key is a 4-amino-acid motif that has been reported to increase helper epitopes' occupancy of the MHC class II molecules and enhance CD4 T cell responses. Ii-Key hybrids are much more potent than epitope-only peptides, both in vitro and in animal studies in vivo, when used in conjunction with epitopes relevant to different diseases [Humphreys, R. E. et al., supra; Gillogly, M. E., et al., *Cancer Immunol Immunother* 53:490-496 (2004); Kallinteris, N. L., et al., *Vaccine* 21:4128-4132 (2003); Kallinteris, N. L., et al., *Vaccine* 23:2336-2338 (2005); Kallinteris, N. L., et al., *J Immunother* 28:352-358 (2005)]. In vitro, some hybrids have been shown to enhance presentation of an antigenic epitope up to 250 times above the baseline stimulation observed using the free antigenic peptide [Humphreys, R. E., et al., supra]. By enhancing the ability of peptide epitopes to charge MHC class II molecules directly on the cell surface, Ii-Key hybrid technology opens the door to a potent and clinically practical strategy for peptide immunotherapy.

Another challenge specific to cancer immunotherapy is that tumor antigens are usually tolerated as self by the immune system. Therefore, the main task of clinical immunologists is to break down tolerance to specific, tumor-associated self-antigens [Touloukian, C. E., et al., *J Immunol* 164:3535-3542 (2000); Knutson, K. L et al., supra; Phan, G. Q., et al., supra; Brinkman, J. A., et al., supra; Hersey, P., et al., supra]. We propose that the ability of Ii-Key hybrids to enhance activation of Th1 CD4+ cells will help greatly to break tolerance to tumor antigens. In our in vitro and in vivo animal studies using Ii-Key/gp100(46-58) and Ii-Key/HER-2/neu(777-789) hybrids [Kallinteris, N. L., et al., *Vaccine* 23:2336-2338 (2005); Kallinteris, N. L., et al., *Frontiers in Bioscience:* 46-58 (2006)], significantly stronger CD4+ T cell activity was obtained. Furthermore, the use of Ii-Key hybrids with inflammatory cytokines or adjuvants is expected to enhance the activity of hybrids and likewise help to breakdown tolerance against tumor antigens.

In order to assess the activity of Ii-Key hybrids in human cells, an Ii-Key/HER-2/neu(777-789) epitope hybrid was used to stimulate lymphocytes from both a healthy donor and a patient with HER-2/neu positive metastatic breast carcinoma. The in vitro proliferation and Interferon (IFN)-γ release was more strongly stimulated by the Ii-Key hybrid than by the epitope-only peptide [Gillogly, M. E et al., supra]. Subsequent studies, using Peripheral Blood Mononuclear Cells (PBMC) from more than 20 patients with HER-2/neu-positive cancer, have confirmed the increased T helper activity of Ii-Key/HER-2/neu hybrids relative to epitope-only peptide in stimulating CTL effectors [Sotiriadou, N. N., et al. Cancer Immunology Immunotherapy, in press (online Sep. 8, 2006)].

Life threatening diseases such as cancer demand new efforts toward effective vaccine design. Peptides represent a simple, safe, and adaptable basis for vaccine development. However, the potency of peptide vaccines is insufficient in most cases for significant therapeutic efficacy. The discovery of Ii-Key is of significant importance in designing potent peptide vaccines. The MHC class II/epitope complex is relatively stable [Fleckenstein, B., et al., *Semin Immunol* 11:405-416 (1999); Joshi, R. V., et al., *Biochemistry* 39:3751-3762 (2000)]. Ii-Key (LRMK (SEQ ID NO: 2)) facilitates the direct loading of epitopes to the MHC class II molecule groove. Without Ii-Key, peptide epitopes have difficulty displacing the pre-bound ambient peptides on MHC class II molecules at the cell surface. With the help of Ii-Key, however, the peptide-binding groove on MHC class II molecules can be opened and closed easily, offering an efficient method to enhance the binding of vaccine peptides to MHC class II molecules. Linking the Ii-Key moiety to an MHC class II epitope, to generate an Ii-Key/MHC class II epitope hybrid, greatly enhances the vaccine potency of the tethered epitope.

This type of vaccine development technology could greatly benefit tumor immunotherapy. Peptides represent the safest form of all vaccine modalities, as they are comprised of the minimal elements required for generation of an effective immune response: MHC class I and/or class II epitopes. However, while immune responses have been observed using peptide vaccines, the demonstration of clinical efficacy is rare, pointing to the need for increased potency. Although peptide vaccine research initially focused on MHC class I epitopes to induce CTL activity, MHC class II epitope vaccines for the induction of Th cell activity have drawn growing attention [Wang, R. F., *Immunol Rev* 188:65-80 (2002); Sette A., and Fikes, J., *Curr Opin Immunol* 15:461-470 (2003); Hanson, H. L. et al., *J Immunol* 172:4215-4224 (2004); Wong, R., et al., *Clin Cancer Res* 10:5004-5013 (2004)]. Recent data has clearly shown that CD4+ Th cell activation is required for the induction of a potent immune response against an immunogen. Antigen-specific Th cells are needed for full activation of antigen-specific CD8+ CTLs and to provide long-term antigen-specific memory [Hung, K., et al., *J Exp Med* 188:2357-2368 (1998); Surman, D. R., et al., *J Immunol* 164:562-565 (2000); Welsh, R. M., et al., *Annu Rev Immunol* 22:711-743 (2004)].

CD4+ Th cells play a critical role by inducing and maintaining both CD8+ T cell and B cell responses and in maintaining immunological memory [Hung, K., et al., *J Exp Med* 188:2357-2368 (1998); Surman, D. R., et al., *J Immunol* 164:562-565 (2000); Welsh, R. M., et al., *Annu Rev Immunol* 22:711-743 (2004), Knutson, K. L. and Disis, M. L., *Cancer Immunol Immunother* (2005); Rocha B. and Tanchot, C., *Curr Opin Immunol* 16:259-263 (2004); Janssen, E. M., et al., *Nature* 434:88-93 (2005); Dissanayake, S. K., et al., *Cancer Res* 64:1867-1874 (2004)]. For example, F. Ossendorp et al. established that tumor antigen-specific Th cells are required for optimal induction of CTLs against MHC class II-negative tumors [*J Exp Med* 187:693-702 (1998)]. The role of CD4+ Th cells in cancer immunity is further highlighted by significant clinical results obtained in melanoma patients receiving adoptive transfer of highly reactive CD8+ and CD4+ T cells [Dudley, M. E., et al., *Science* 298:850-854 (2002); Robbins, P. F., et al., *J Immunol* 169:6036-6047 (2002)]. F. G. Gao et al. showed that in order to activate memory CD8+ T cells to become fully functional tumor killer cells, antigen-specific CD4+ Th cells were required [*Cancer Res* 62:6438-6441 (2002)]. P. Yu et al. defined how the complementary role of CD4+ Th cells is required for efficient cross-presentation of tumor antigens to CD8+ T cells [*J Exp Med* 197:985-995 (2003)]. Furthermore, CD4+ T cells can help to break down tolerance to persistent self-antigens (e.g., tumor-associated antigens) to fight established tumors in an Interleukin (IL)-2 dependent mechanism [Anthony, P. A., et al., *J Immunol* 174:2591-2601 (2005)]. Along with the continuing discovery of novel defined epitopes, the investigation of MHC class II epitope-based vaccines in tumor immunotherapy is advancing [Wang, R. F., supra; Sette A., and Fikes, J., supra; Hanson, H. L. et al., supra; Wong, R., et al., supra; Mandic, M., et al., *J Immunol* 174:1751-1759 (2005); Lu, J., et al., *J Immunol* 172:4575-4582 (2004); Slager, E. H., et al., *J Immunol* 172: 5095-5102 (2004)].

Conventional peptide vaccines have a number of disadvantages. First, they do not stimulate CD4+ T lymphocyte responses, which leads to a lack of B cell response and a lack of immunologic memory. Second, they are not well processed by the immune system. Therefore, clinically, these vaccines require coadministration with immune stimulants such as Granulocyte Monocyte-Colony Stimulating Factor (GM-CSF). More importantly, the vaccines are of limited use, restricted to only those patients with HLA A-2 subtype, an HLA phenotype which occurs only in about 50% of the population but which most efficiently processes these peptides for antigen expression.

Several methods such as LEAPS and ISCOMATRIX have been developed to enhance the potency of peptide vaccines. A variety of techniques have been explored to improve the activity of peptide vaccines but none are MHC class II epitope-specific. These methods use different mechanisms for peptide vaccine enhancement. Improving the delivery of MHC class II epitopes into APCs is a common approach to enhancing MHC class II peptide vaccines. For example, exosomes are used as a delivery vehicle for better activation of both CD8+ and CD4+ T cells [Delcayre, A. and Le Pecq, J. B., *Opin Mol. Ther.* 8:31-8 (2006)]. Another method is ISCOMATRIX which is a cage-like structure composed of antigens, such as peptides, and adjuvants [Sanders, M. T., et al., *Immunol Cell Biol.* 83:119-28 (2005)]. ISCOMATRIX effectively induces both humoral and cellular immune responses against the antigens incorporated in the structure by enhancing the delivery of peptide antigens and by providing adjuvant stimulation. APCs usually have difficulty acquiring soluble antigen. Antigen/antibody complexes are more accessible to APCs through the recognition of the Fcy receptor on APCs by the Fc domain on an antibody [Nagata, Y., et al., *Proc Natl Acad Sci USA* 99:10629-34 (2002)]. Molecular chaperones are necessary components for better binding of epitopes to MHC class II molecules. Bacterial HSP 70 enhances the immune response against MHC class II epitopes complexed to bacterial HSP70 [Tobian, A. et al., *J Immunol* 172:5277-86 (2004)]. However, the enhancement occurs only at low pH, indicating that chaperone-complexed epitope binding to MHC class II is also limited by CLIP [Urban, R. G., et al., *Exp Med* 180:751-755 (1994)]. More recently, peptide conjugates targeting specific components of immune cells have been investigated. An example of the latter employs a T cell-binding ligand coupled to a peptide antigen (Ligand Epitope Antigen Presentation System, LEAPS) [Zimmerman, D. H. and Rosenthal, K. S., *Front Biosci* 10:790-798 (2005)]. Because Ii-Key hybrids target the charging of MHC class II molecules, antigen presentation to T cells is more selective than LEAPS technology. Peptide vaccines are usually limited by polymorphic MHC class II allele restrictions. A non-specific T helper epitope technology, the pan-DR epitope (PADRE), has also been developed to circumvent this limitation [Franke, E. D., et al., *Vaccine* 17:1201-5 (1999)]. The advantage of PADRE is that it overcomes restrictions by HLA-DR alleles. DNA vaccines using the Ii gene as a delivery carrier to deliver T helper epitope to MHC class II molecules have been developed [Nagata, T et al., *Vaccine* 20:105-14 (2001)]. This method utilizes an Ii gene in which the CLIP portion has been replaced by a DNA fragment encoding a MHC class II epitope. This method has successfully induced epitope-specific CD4+ T cells. It should also be noted that Ii-Key hybrid technology is compatible with many of the methods discussed to further enhance the overall antigen-specific response. For example, Ii-Key hybrid peptides might be incorporated into ISCOMATRIX to further enhance the potency of the vaccine.

A hybrid peptide of a Her-2/neu antigenic epitope p776-790 and the Ii-Key protein has been developed. This hybrid protein, called AE37, brings the antigenic epitope into close proximity of the target binding site on class II MHC molecules, thus priming the molecule for antigen presentation. We have performed a phase Ib trial of the AE37 peptide vaccine in human Her-2/neu+ breast cancer patients to document toxicity and measure immunologic responses to escalating doses of the vaccine. The results of this trial are presented here.

SUMMARY OF THE INVENTION

In one aspect, the present invention involves methods to treat cancer in humans, the cancer being characterized by expression of the Her-2/neu protein. The methods include the treatment of breast cancer. The methods entail providing an Ii-Key/MHC class II hybrid construct and stimulating a patient's immune system by vaccination with the hybrid construct. Vaccination with the hybrid construct stimulates CD 4+ T cell activation and supports a CTL response specific to the native Her-2/neu protein.

In another aspect, the invention involves pharmaceutical compositions for use in the treatment of cancer. A composition of the invention comprises the hybrid construct in a pharmaceutically acceptable carrier. The hybrid construct includes the LRMK (SEQ ID NO: 2) residues of the Ii protein linked to the N-terminus of an MHC class II epitope of Her-2/neu or a DNA encoding the same peptide. The Her-2/neu epitope included in the construct may be GVGSPYVSR-LLGICL (SEQ ID NO: 3). The composition may further comprise an adjuvant which may be GM-CSF.

BRIEF DESCRIPTION OF THE DRAWINGS

FIG. 1: Patients were vaccinated with 100 μg AE37 peptide plus 250 μg GM-CSF, monthly, for six months.

FIG. 2: Patients were vaccinated with 500 μg AE37 peptide plus 250 μg GM-CSF initially. A GM-CSF reduction was necessary in all patients by dose R3.

FIG. 3: Patients were initially vaccinated with 1000 μg AE37 peptide without GM-CSF. Patient A9V9 was given an increased dose of GM-CSF beginning at dose R4.

FIG. 4: The same patients from FIG. 3 were initially vaccinated with 1000 μg AE37 peptide. Patients A7V7 and A8V8 were given a decreased dose of AE37 by dose R4.

FIG. 7: PBMC's were stimulated with 2.5 μg AE37 peptide.

FIG. 8: PBMC's were stimulated with 25 μg AE37 peptide.

FIG. 9: PBMC's were stimulated with 2.5 μg AE36 peptide.

FIG. 10: PBMC's were stimulated with 25 μg AE36 peptide.

FIG. 11: PBMC's were stimulated with 1.0 μg AE37 peptide.

FIG. 12: PBMC's were stimulated with 1.0 μg AE36 peptide.

FIG. 13: PBMC's were stimulated with 10 μg AE37 peptide.

FIG. 14: PBMC's were stimulated with 10 μg AE36 peptide.

FIG. 15: PBMC's were stimulated with 1.0 μg AE37 peptide.

FIG. 16: PBMC's were stimulated with 1.0 μg AE36 peptide.

FIG. 17: PBMC's were stimulated with 10 μg AE37 peptide.

FIG. 18: PBMC's were stimulated with 10 μg AE36 peptide.

DETAILED DESCRIPTION OF THE INVENTION

The hybrid vaccine composition and methods of use disclosed herein have been designed to overcome the shortcomings of conventional peptide vaccines. By taking advantage of the Ii-Key protein interaction with Class II MHC molecules, the compositions and methods of the present invention bring the antigenic epitope of Her-2/neu to the Class II MHC binding groove, bypassing the normal antigen processing pathway. In this context, antigen can then be presented to the immune system, stimulating a specific CD4+ T lymphocyte response. Due to the increased potency of Ii-Key/MHC class II hybrids in stimulating immune response, less efficiency in the process can be tolerated, and use of the vaccine does not have to be limited to HLA A-2 patients, and it may not require the use of immune system stimulants.

Described herein is a method of treating a cancer in humans, the cancer being characterized by expression of Her-2/neu. As noted in the Background section, cancers which express Her-2/neu include breast, ovary, recto-colon, lung, prostate, stomach, pancreatic, and biliary cancers. The method comprises providing an Ii-Key/MHC class II hybrid construct in a pharmaceutically acceptable carrier and vaccinating a patient with the hybrid, under conditions appropriate for the stimulation of an immune response. The hybrid construct may be administered as an Ii-Key hybrid peptide or in the form of a nucleic acid encoding an Ii-Key hybrid peptide. The Ii-Key/MHC class II hybrid peptide comprises the LRMK (SEQ ID NO: 2) amino acid residues of the Ii protein linked to the N-terminus of an MHC class II epitope containing segment of Her-2/neu. The LRMK (SEQ ID NO: 2) residues and the MHC class II epitope should be separated by a distance equivalent to the length of about two to twenty amino acid residues. This space can contain a variety of linkers, including a simple polymethylene (ava) linker, the natural sequence of Ii extending from the C-terminus of LRMK (SEQ ID NO: 2), or the natural sequence of Her-2/neu extending from the N-terminus of the MHC class II epitope. The method results in the stimulation of a CD4+ T cell response. Similarly, the hybrid construct can be administered in the form of a nucleic acid encoding an Ii-Key/Her-2/neu hybrid peptide.

Figure 16:
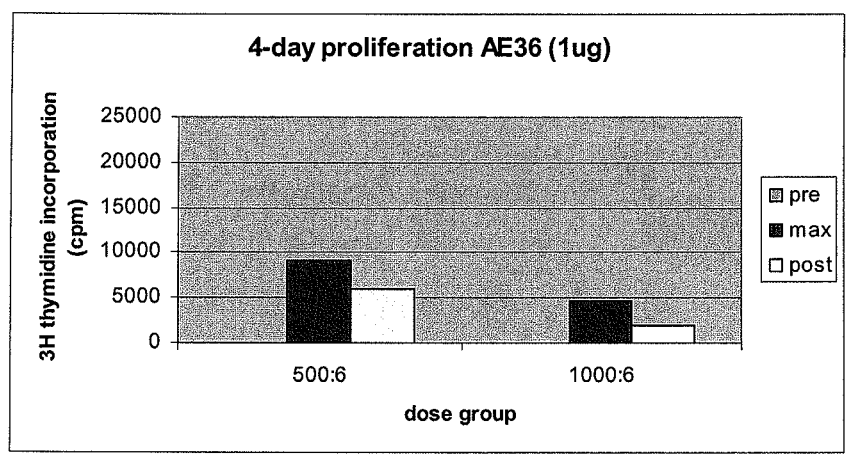
Figure 17:
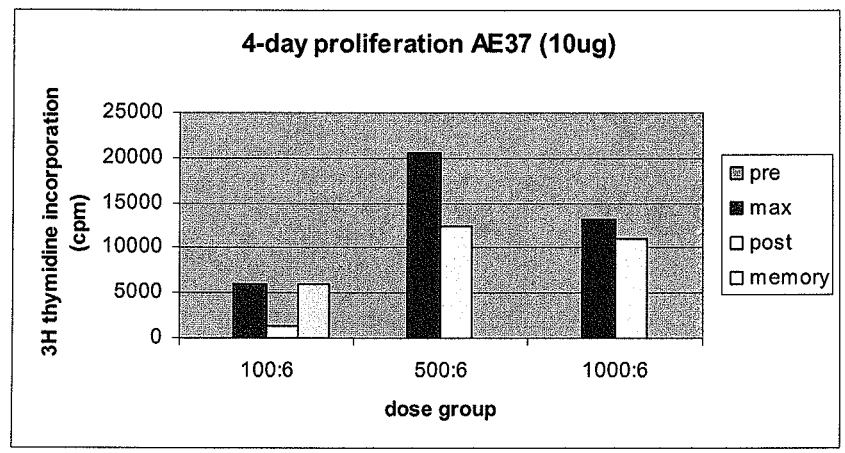
Figure 18:
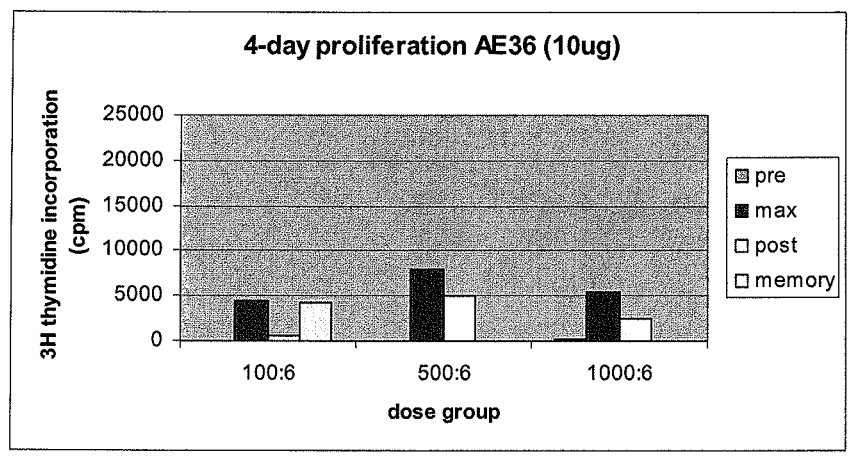

As is detailed in the Exemplification section, human cancer patients were vaccinated with AE37, a hybrid Ii-Key/Her-2/neu MHC class II peptide. PBMC's were drawn from the patients and analyzed using IFN-γ ELISPOT and peptide-specific Proliferation assays. The ELISPOT analysis showed (see FIGS. 9, 10, 12, and 14) that patients exhibited an increased CD4+ T cell response to AE36, the native Her-2/neu MHC class II peptide, after being vaccinated with the Ii-Key/Her-2/neu hybrid peptide. The Proliferation Assay showed that CD4+ T cells had increased capacity to divide and expand a specific clone that recognized the native Her-2/neu MHC class II peptide (see FIGS. 16 and 18).

The method of the present invention includes treating a cancer patient by vaccination with an Ii-Key/Her-2/neu hybrid construct whereby the stimulation of a CD4+ T cell response specific to native Her-2/neu peptide is enhanced. The ELISPOT and Proliferation assays show increased CD4+ T cell response to the native Her-2/neu peptide but not to the non-Her-2/neu negative control peptide AEN (data not shown) in patients vaccinated with the Ii-Key/Her-2/neu hybrid construct.

The method of the present invention includes treating a cancer patient by vaccination with an Ii-Key/MHC class II hybrid construct wherein the MHC class II epitope is contained within the peptide GVGSPYVSRLLGICL (SEQ ID NO: 3). The method comprises treating a cancer patient by vaccination with a hybrid peptide with the amino acid sequence LRMKGVGSPYVSRLLGICL (SEQ ID NO: 4) or by vaccination with a DNA encoding the same. The Patient characteristics and clinical protocols section of the Exemplification discloses the amino acid sequences used for the MHC class II epitope containing segment and the peptide used in the AE37 vaccine.

The patients used in this study were breast cancer patients, therefore the method of the invention includes the treatment of breast cancer patients by vaccination with an Ii-Key/Her-2/neu hybrid peptide or with a DNA encoding the same. Since other cancers are known to express Her-2/neu, it will be readily apparent to a person having ordinary skill in the art that the preceding method may be implemented in the treatment of not only breast cancer but of any cancer which expresses Her-2/neu. Thus the invention includes methods of treating ovary, recto-colon, lung, prostate, stomach, pancreatic, or biliary cancers by vaccination with an Ii-Key/Her-2/neu hybrid peptide.

In another embodiment, the present invention provides a pharmaceutical composition, for use in the treatment of cancer, comprising an Ii-Key/MHC Class II hybrid construct in a pharmaceutically acceptable carrier. A critical requirement of a pharmaceutical composition intended for use in humans is safety. The Exemplification Section includes experiments demonstrating safety in humans. The Ii-Key/MHC Class II hybrid construct comprises the LRMK (SEQ ID NO: 2) residues of the Ii protein linked to the N-terminus of an MHC Class II epitope-containing segment of Her-2/neu. The LRMK (SEQ ID NO: 2) residues and the MHC class II epitope should be separated by a distance equivalent to the length of about two to twenty amino acid residues. This space can contain a variety of linkers, including a simple polymethylene (ava) linker, the natural sequence of Ii extending from the C-terminus of LRMK (SEQ ID NO: 2), or the natural sequence of Her-2/neu extending from the N-terminus of the MHC class II epitope. The Ii-Key/MHC Class II hybrid construct can also comprise a DNA encoding the same hybrid peptide. More specifically the present invention includes a composition wherein the MHC Class II epitope of the hybrid construct is contained within the peptide GVGSPYVSRLLGICL (SEQ ID NO: 3). The composition of the present invention includes the hybrid construct comprising amino acids having the sequence LRMKGVGSPYVSRLLGICL (SEQ ID NO: 4) or a DNA encoding the same. The results in the Exemplification of the ELISPOT and Proliferation assays show that human cancer patients vaccinated with Ii-Key/Her-2/neu hybrid constructs exhibit an increased CD4+ T cell response to native Her-2/neu peptide.

The present invention further provides a pharmaceutical composition, for use in the treatment of cancer, comprising an adjuvant and an Ii-Key/MHC Class II hybrid construct in a pharmaceutically acceptable carrier. The Ii-Key/MHC Class II hybrid construct comprises the LRMK (SEQ ID NO: 2) residues of Ii-Key protein linked to the N-terminus of an MHC Class II epitope containing segment of Her-2/neu. The construct can also comprise a DNA encoding the same hybrid peptide. The composition provided may include the adjuvant GM-CSF. The Vaccine and Vaccination Series sections of the Exemplification and FIGS. 1-4 describe the inclusion of an adjuvant, GM-CSF, in the hybrid construct compositions administered to the cancer patients in the clinical trial. The ELISPOT and peptide-specific Proliferation assays disclose that patients receiving a composition comprising an Ii-Key/Her-2/neu hybrid construct and an adjuvant show increased immunologic responses.

Ii-Key/MHC class II hybrid vaccines can induce long-term, antigen-specific CD4+ T cell stimulation. The enhanced Th cell activation afforded by hybridization with Ii-Key represents an important advance in the design of peptide vaccines. Furthermore, the antigen-specific mechanism of T helper stimulation allows Ii-Key hybrid technology to be used together with other strategies (such as ISCOMATRIX) to further enhance the potency of the MHC class II vaccine peptides.

It will be recognized by one skilled in the art that the hybrid construct composition may be administered in the form of an Ii-Key hybrid peptide or as a nucleic acid construct encoding an amino-acid-based Ii-Key hybrid peptide. One skilled in the art, using routine experimental methods, could also substitute various natural or non-natural amino acids at respective residue positions in the hybrid peptide. Some examples of molecules which may be substituted are peptidomimetic structures, D-isomer amino acids, N-methyl amino acids, L-isomer amino acids, modified L-isomer amino acids, and cyclized derivatives.

The invention now being fully described, it will be apparent to one of ordinary skill in the art that many changes and modifications can be made thereto without departing from the spirit or scope of the invention.

EXEMPLIFICATION

Patient Characteristics and Clinical Protocols

The Walter Reed Army Medical Center Department of Clinical Investigation approved the clinical protocol. This clinical trial is being conducted under an investigational new drug application (IND12229) approved by the Food and Drug Administration. All patients had histologically confirmed node negative breast cancer (NNBC) that expressed HER-2/neu by standard immunohistochemistry. All patients had completed a standard course of surgery, chemotherapy, and radiation therapy (as required) before enrollment, and those patients on chemoprevention continued on their specific regimens. After screening for eligibility criteria and proper counseling and consenting, patients with NNBC were enrolled into the study and HLA typed. HLA A2− patients and HLA A2+ patients who were not interested in an alternative vaccine trial were vaccinated. Before vaccination, patients were skin tested with a panel of recall antigens (Mantoux test: mumps, tetanus, and Candida). Patients reacting (>5 mm induration) to at least two antigens were considered immunocompetent.

To investigate the safety of the AE37 hybrid vaccine, we have thus far enrolled 15 patients with NNBC who were disease-free after standard therapy. The dose escalation safety trial design is for five groups of three patients to receive escalating doses of AE37 with or without GM-CSF in six monthly inoculations. An additional six patients will be vaccinated at the optimal biologic dosing (OBD) in order to complete the 21 patient phase I trial. Enrolled patients were HLA typed, and HLA-A2$^-$ patients and those HLA-A2$^+$ patients not interested in an alternative vaccine trial were vaccinated. Table 2 shows patient demographics.

TABLE 2

Patient demographics (n = 15 unless specified)

| | |
|---|---|
| Median age, years | 56 |
| Range, years | 44-70 |
| Race | |
| White | 60 |
| Black | 33 |
| Asian | 7 |
| Tumor size* | |
| T1, % | 89 |
| T2-T4, % | 11 |
| Histological grade* | |
| I-II, % | 67 |
| III, % | 33 |
| ER-negative, PR-negative, %* | 22 |
| No chemotherapy, % | 80 |
| No XRT, % | 23 |
| No hormonal therapy, % | 20 |

*n = 18 (total number of tumors in 15 patients); ER = Estrogen Receptor; PR = Progesterone Receptor Vaccine The Ii-Key/HER-2/neu MHC class II Peptide, AE37 (Ac-LRMKGVGSPYVSRLLGICL-NH$_2$ (SEQ ID NO: 4)) was commercially produced in good manufacturing practices (GMP) grade by NeoMPS Inc (San Diego, Calif.). Peptide purity was verified by high-performance liquid chromatography and mass spectrometry, and the amino acid content was determined by amino acid analysis. The peptide was purified to more than 95%. Sterility and general safety testing was carried out by the manufacturer and conformed to FDA requirements. Lyophilized peptide was reconstituted in sterile saline at the following concentrations: 100 μg in 0.5 ml; 500 μg in 0.5 ml; and 1 mg in 0.5 ml. Vaccine was mixed with GM-CSF (Berlex, Seattle, Wash.) at varying concentrations (see below) in 0.5 ml. The 1.0-ml inoculation was divided and given intradermally at two sites (split injection) within 5 cm of each other. All inoculations were given in the same extremity.

Vaccination Series

The study was performed as a two-stage safety trial to define the maximum tolerated dose of vaccine as well as the optimal dosing of the vaccine and GM-CSF. In the first stage (FIGS. 1-4), patient dose groups were given escalating amounts of the AE37 peptide. Three patients were assigned to each dosing group and were given the assigned dose of AE37 with a fixed initial dose of GM-CSF of 250 μg. This dose of GM-CSF was chosen based on our previous E75 trials. However, GM-CSF was reduced 50% for subsequent inoculations when local skin reaction exceeded 100 mm. All patients received monthly inoculations for six months. Dosing groups were as follows (AE37 (μg):#inoculations): 100:6, 500:6, 1000:6. Because each patient in the 500:6 group required significant and repeated reductions of GM-CSF, the 1000:6 group was initially inoculated without GM-CSF; GM-CSF was added back if local reaction from the two injection sites were non-confluent.

In the second stage of the trial, optimal dosing of GM-CSF was assessed with a fixed dose of AE37. Given the dose reductions required with the 1000:6 dose group, we chose 500 μg as the fixed AE37 dose. Three additional groups of three patients each were inoculated with 500 μg vaccine with decreasing initial doses of GM-CSF to determine the optimal combination dosing. These groups were as follows (AE37 (μg):initial GM-CSF dose (μg)): 500:125, 500:30, and 500:TBD. If the 500:30 dose is tolerated for the complete series and produces a good local reaction in all three patients, then this dose will be the optimal biologic dose (OBD) and an additional three patients will be inoculated with this regimen. However, if any patient requires a dose escalation of the GM-CSF dose, then an additional group will be added, 500:62.5. Alternatively, if any patient does not tolerate the 500:30 and requires removal of the GM-CSF, then an additional group will be added, 500:0.

TABLE 1

Dosing of vaccine and adjuvant

| Dose Group | Patient number | AE37 dose (μg) | GM-CSF initial dose (μg)* | Schedule |
|---|---|---|---|---|
| Stage I | | | | |
| 100:6 | A1, A2, A3 | 100 | 250 | Monthly × 6 |
| 500:6 | A4, A5, A6 | 500 | 250 | Monthly × 6 |
| 1000:6 | A7, A8, A9 | 1000 | 0 | Monthly × 6 |
| Stage II | | | | |
| 500:125 | A10, A11, A12 | 500 | 125 | Monthly × 6 |
| 500:30 | A13, A14, A15 | 500 | 30 | Monthly × 6 |
| | (A16-18 if OBD) | 500 | | Monthly × 6 |
| Possible | | | | |
| 500:62.5 | (A16-18) | 500 | 62.5 | Monthly × 6 |
| 500:0 | (A16-18) | 500 | 0 | Monthly × 6 |

*If patient's local reaction measured >100 mm, then GM-CSF (or peptide if no GM-CSF given) dose was reduced 50%.

The hybrid peptide AE37 was mixed with GM-CSF (varying doses) and injected intradermally in the same extremity on a monthly basis. Each dosing group consisted of 3 patients. Patients were enrolled sequentially; however, if a patient failed to complete a series, a replacement patient was given the same dose until each group was complete. Table 1 provides the two-stage safety and dose-escalation schedule. Stage I was designed to identify the maximum tolerated dose of vaccine. Stage II was designed to find the optimal biologic dose. Local toxicity dictated dose adjustments in each stage.

A local reaction ≥100 mm in at least one direction necessitates a reduction of GM-CSF dose for the subsequent vaccination (or reduction in vaccine dose if patient received no GM-CSF). The first group (100:6) required no reductions in dose. However, each patient in the second group (500:6) required a GM-CSF dose reduction by the third vaccine. FIGS. 1-4 show the dose of GM-CSF and the local reaction in each patient throughout the vaccine series. Given the robust local reactions, the third group (1000:6) was initiated without any GM-CSF; two of the three patients in this group required reduction of vaccine dose on multiple occasions. The third patient in this group did not show robust local response and GM-CSF was added back to her vaccine schedule in an escalating fashion.

Based on the findings in the first stage, stage II was initiated with patients scheduled to receive the vaccine at a fixed dose (AE37=500 µg) with different doses of adjuvant to find the optimal combination. Dose reductions of GM-CSF were again dictated by a local reaction in any dimension ≥100 mm.

Toxicity

The National Institutes of Health Common Toxicity Criteria (CTC) (Version 2, Mar. 23, 1998) definitions of adverse events were applied. Both local toxicity at the injection sites as well as systemic toxicity were evaluated in all patients for all inoculations. By design, progression to the second stage occurred only if no significant toxicity occurred in the first stage.

After each vaccination, the patients were observed for 1 hour for signs of a hypersensitivity reaction; they returned 48-72 hours later to be questioned regarding local and systemic reactions and have their injection sites checked. Toxicities were graded per the National Institutes of Health Common Toxicity Criteria and reported on a scale zero to five (Table 3). Local toxicity dictated dose reductions as described above. All patients had grade 1 or 2 local toxicity (desired effect) and no grade 3 or greater local toxicities have been reported. Only grade 1 systemic toxicities were reported. So far, 12 patients have completed the vaccine series and their have been no patient withdrawals from the trial.

Control Peptides and Proteins

The AE37 peptide used in this study is a fusion/hybrid of the Ii-Key peptide (LRMK (SEQ ID NO: 2)) with the native HER-2/neu peptide (aa776-790: GVGSPYVSRLLGICL (SEQ ID NO: 3)). In order to assess/determine that immune responses being measured/monitored are representative/indicative of reactivity against the native HER-2/neu peptide, we synthesized the native peptide, Her-2/neu MHC class II Peptide, AE36 (Ac-GVGSPYVSRLLGICL-NH$_2$ (SEQ ID NO: 3)). In addition, a negative control peptide, AEN, containing the Ii-Key peptide fused to a non-HER-2/neu sequence (Ac-LRMK-ava-YVDRFYKTLRAEQ-NH$_2$(SEQ ID NO: 5)) was also used in some of the immune assays. The non-HER-2/neu sequence is that of a promiscuous class II peptide from the HIV gag protein. Tetanus Toxoid (TT) (List Biologicals Inc) was used as a positive control antigen for the immune assays.

Peripheral Blood Mononuclear Cell (PBMC) Isolation and Cultures

Blood was drawn from patients prior to receiving each inoculation, at one month (post-vaccination), and at six months (long-term) after completing the series. Forty ml of peripheral blood was drawn into Vacutainer® CPT™ tubes (Becton Dickinson, Franklin Lakes, N.J.) and centrifuged for the isolation of PBMC populations. PBMC were washed in HBSS and re-suspended in culture medium (CM) consisting of RPMI-1640 containing 10% FCS (Gemini Bio-Products, Woodland, Calif.) supplemented with 1× penicillin/L-glutamine/streptomycin (Life Technologies, Gaithersburg, Md.) and used for setting up the immunomonitoring protocol/assays which consisted of ELISPOT (IFN-γ secretion) and proliferation (3H-thymidine incorporation) assays. All cultures were maintained in a humidified incubator at 37° C. in 5% $CO_2$.

IFN-γELISPOT Assays

ELISPOT assays measure the cytokine secretion of T cells. In order to monitor the ongoing immune response in the patients receiving/to the AE37 vaccination we measured the IFN-γ secretion activity in PBMC cultures stimulated with culture medium (CM), AE36, AE37, AEN or TT using the ELISPOT assay. The ELISPOT assay was set up as a direct or ex vivo ELISPOT assay and a 7-day ELISPOT assay that has been developed in our laboratory.

Ex Vivo IFN-γ—+ELISPOT Assay

The human IFN-γ ELISPOT Kit (BD-Pharmingen) was used for the ELISPOT assays. 100 µl aliquots of CM containing 40 ng/ml of recombinant human IL-7 (R&D Systems, MN) were added to 8 wells of an ELISPOT plate. The plate was placed in a $CO_2$ incubator for a period of at least 30 minutes. During this time the PBMC population prepared from the patient's peripheral blood (as described in the previous section) was resuspended at 5×10$^6$ cells/ml in CM and added as 100 µl aliquots to 8 polystyrene tubes (BD-Falcon, N.J.). Each peptide (AE36 or AE37 or AEN) or antigen (TT) was added to a separate tube while one tube had no stimulant added to it and this served as the CM control tube. The AE37 and control peptides and antigen were added in the following

TABLE 3

Maximum Toxicity

| Patient | Local Toxicity | | | Systemic Toxicity | | |
|---|---|---|---|---|---|---|
| | Grade 1 | Grade 2 | Grade 3 | Grade 1 | Grade 2 | Grade 3 |
| Group 1 100 µg AE37 + 250 µg GM-CSF | 1 | 2 | 0 | 3 | 0 | 0 |
| Group 2 500 µg AE37 + 250 µg GM-CSF | 0 | 3 | 0 | 2 | 0 | 0 |
| Group 3 1000 µg AE37 | 1 | 2 | 0 | 2 | 0 | 0 |
| Group 4 500 µg AE37 + 125 µg GM-CSF | 1 | 2 | 0 | 3 | 0 | 0 |
| TOTAL | 3 (25)% | 9 (75%) | 0 (0%) | 10 (83%) | 0 (0%) | 0 (0%) | amounts: 2.5 μg AEN, 25 μg AEN, 2.5 μg AE36, 25 μg AE36, 2.5 μg AE37, 25 μg AE37, 0.2 μg TT. The aliquots of cell suspensions with the added peptides/antigen were mixed thoroughly and transferred to the respective/separate wells of the ELISPOT plate containing the CM+IL-7 that had been placed earlier in the incubator. The plate was then returned to the incubator for an overnight incubation of approximately 16-18 hours. On the next day the plate was developed as per manufacturers' instructions in the kit. The plate was allowed to dry and the number of spots present in each well was counted and analyzed using a CTL-ImmunoSpot Analyzer (C.T.L. Cellular Technology Ltd, OH) (FIGS. 7-10). The full range of concentrations and peptides tested for each patient varied depending upon the availability of sufficient PBMC yield from the patient's blood sample. Whenever possible the assay was set up in duplicates.

7-Day IFN-γELISPOT Assay

As a method of increasing or expanding the sensitivity and capability of detecting the presence and activity of vaccine-specific T cells being induced in the patients by the AE37 vaccine, we have developed a modified ELISPOT assay that is performed using cells from 7-day cultures that have been stimulated in the absence or presence of the same panel of peptides used in the ex vivo ELISPOT assay. Briefly, each peptide (AE36, AE37 or AEN) or antigen (TT) was added to a separate well of a 48-well plate while one well had no stimulant added to it and this served as the CM control well. The AE37 and control peptides and antigen were added in the following amounts: 1 μg AEN, 10 μg AEN, 1 μg AE36, 10 μg AE36, 1 μg AE37, 10 μg AE37, 1 μg TT. The PBMC population prepared from the patient's peripheral blood (as described in the previous section) was resuspended at $2\times10^6$ cells/ml in CM and added as 1 ml aliquots to the 8 wells. The plate was then incubated in a humidified $CO_2$ incubator for a period of 7 days. At the end of the incubation period the plate was removed and the cells/cultures were harvested into separate tubes, spun down, resuspended in CM, and counted. The separate populations of cells were then added at $1\times10^5$, $2\times10^5$, or $3\times10^5$ cells/100 μl to separate/respective wells of an ELISPOT plate that had been pre-incubated with 100 μl per well of CM (without IL-7) for a minimal time period of 30 minutes. The plate was then returned to the incubator for an overnight incubation of approximately 16-18 hours. On the next day the plate was developed as per manufacturers' instructions in the kit. The plate was allowed to dry and the number of spots present in each well was counted and analyzed using a CTL-ImmunoSpot Analyzer (C.T.L. Cellular Technology Ltd, OH) (FIGS. 11-14). The full range of concentrations and peptides and numbers of cells/well tested for each patient varied depending upon the availability of sufficient cells recovered from the 7-day cultures. Whenever possible the assay was set up in duplicates.

Proliferation Assay

The PBMC population prepared from the patient's peripheral blood sample was also used for the monitoring of vaccine-specific proliferative activity of the T lymphocytes using a standard radioactive $^3$H-thymidine incorporation assay. The proliferation assay measures a T cell's capacity to divide and thus expand a specific clone that recognizes the stimulating antigen. Briefly, the PBMC population was stimulated in the absence or presence of the same panel of peptides used in the ex vivo ELISPOT assay. Each peptide (AE36 or AE37 or AEN) or antigen (TT) was added to 3 separate wells (triplicates) of a 96-round bottom well plate while one set of wells had no stimulant added to it and served as the CM control wells. The AE37 and control peptides and antigen were added in the following amounts: 1.0 μg AEN, 10 μg AEN, 1.0 μg AE36, 10 μg AE36, 1.0 μg AE37, 10 μg AE37, 0.2 μg TT. The PBMC population prepared from the patient's peripheral blood (as described in the previous section) was resuspended at $1.5\times10^6$ cells/ml in CM and added as 200 μl aliquots to the wells. The plate was then incubated in a humidified $CO_2$ incubator for a period of 4 days. On the third day of incubation the plate was removed and the wells were pulsed with 1 μCi/well of radioactive $^3$H-thymidine after which the plate was returned to the incubator. On the fourth day the plate was removed from the incubator and the cells were harvested onto a filtermat using a cell harvester (Harvester96-MachIII, Tomtec, Conn.). The filtermat was dried and placed in a sample bag with scintillation fluid (BetaScint, Perkin-Elmer) and counted using a scintillation counter (MicroBeta Trilux Scintillation Counter, Perkin-Elmer). The proliferative activity associated with the cultures was measured by the amount of thymidine incorporation which was determined as counts per minute (cpm). The average cpm was calculated for the triplicate cultures with the different peptides (FIGS. 15-18). The full range of concentrations and peptides tested and the number of replicate wells for each patient varied depending upon the availability of sufficient PBMC yield from the patient's blood sample.

Immunologic Response; Local Reaction; Delayed Type Hypersensitivity (DTH)

A direct in vivo measure of the vaccine's effectiveness is the DTH reaction. Patients were injected intradermally with 100 μg of AE37 (without GM-CSF) prior to the initiation of the vaccination series and one month after the completion of the vaccination regimen in the opposite limb to which they received the vaccine series. Patients were also injected intradermally with a parallel control (sterile saline, same volume) at a site on the back or extremity (opposite side from the vaccination site). The DTH reaction was measured in two dimensions at 48-72 hours using the sensitive ballpoint pen method and compared with control. Pre- and post-vaccination DTH reactions were also compared.

Figure 1:
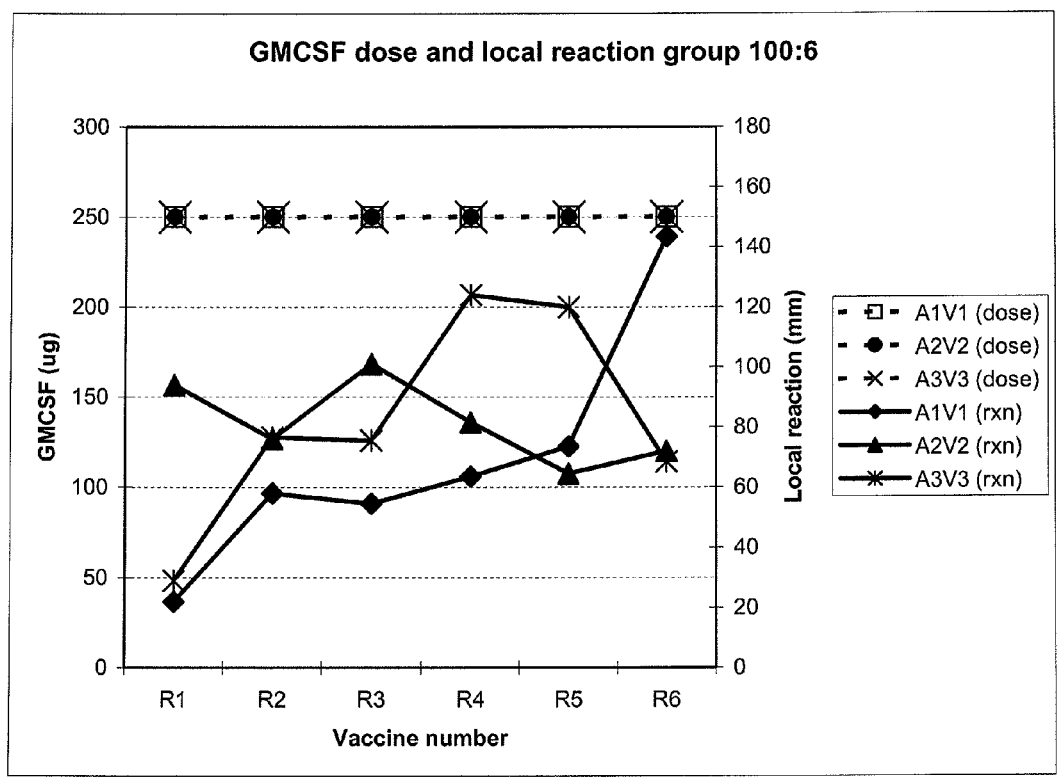
FIGS. 1-4: Diagrams represent the local DTH reaction (solid lines) and dose of GM-CSF (dashed lines). Patients were vaccinated monthly, for six months, with peptide plus GM-CSF in different dose groups. Each patient was evaluated 48-72 hours later for local and systemic toxicity. A local reaction exceeding 100 mm induration necessitated a dose reduction in the GM-CSF for subsequent vaccinations.
Figure 2:
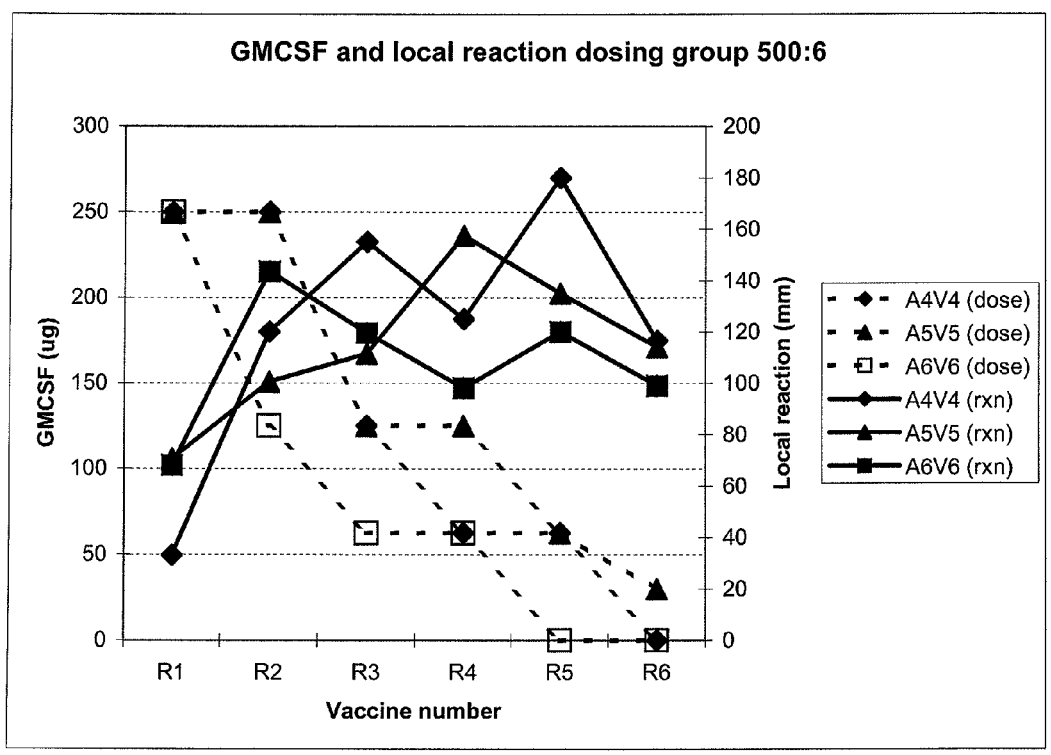
Figure 3:
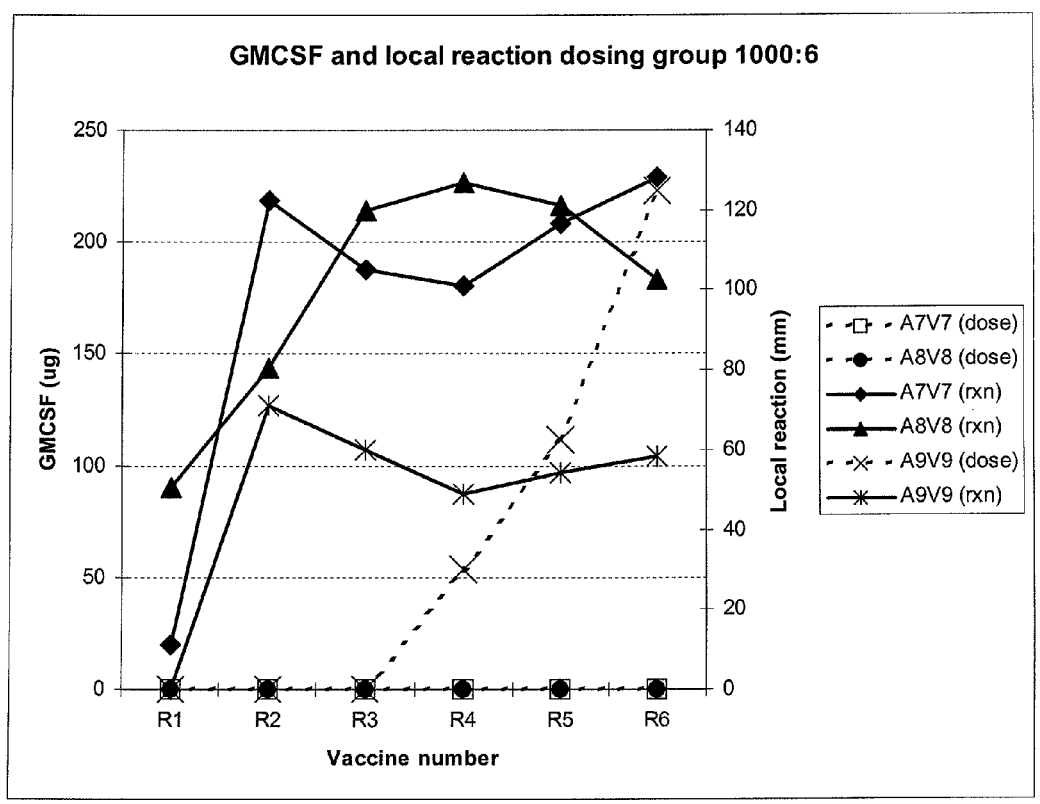
Figure 4:
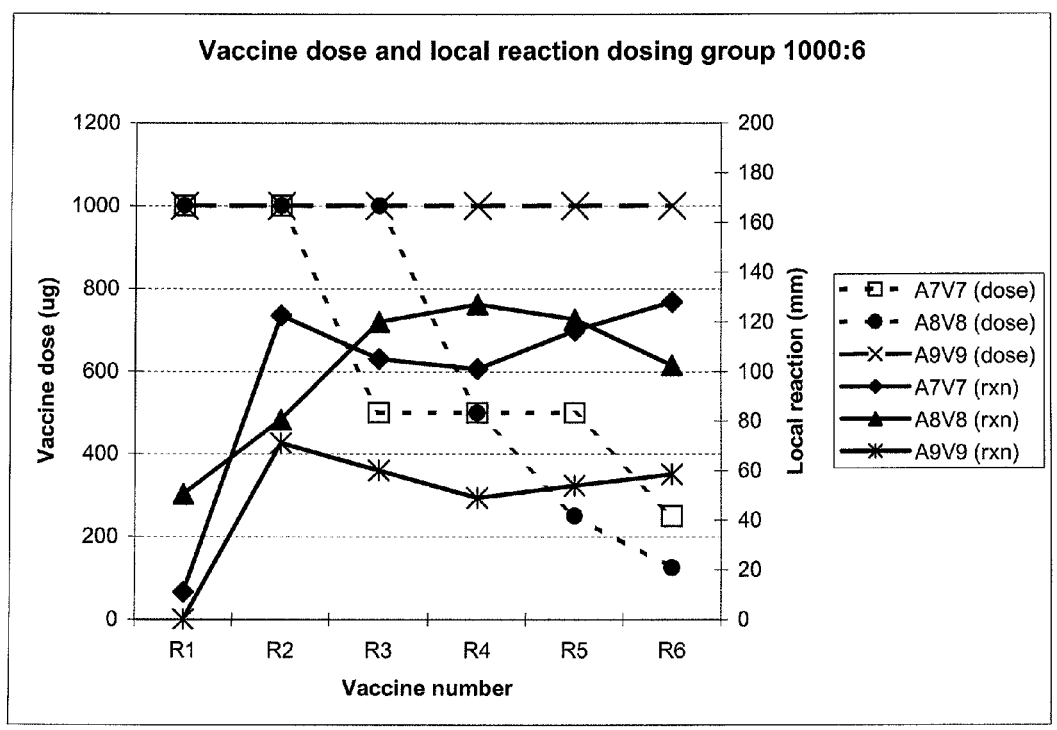
Figure 5:
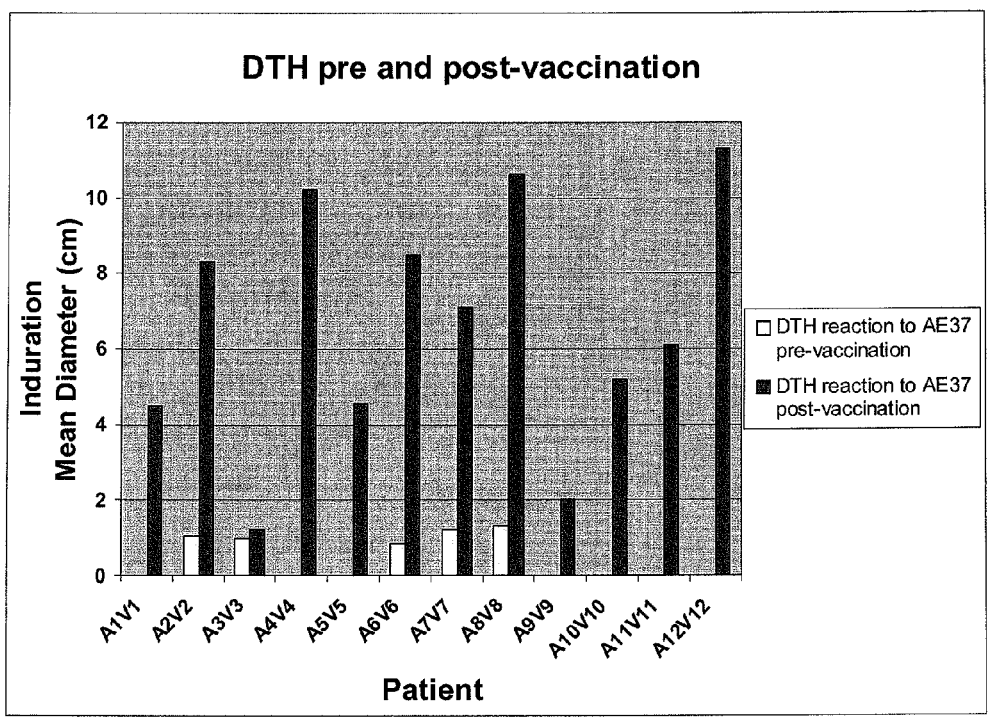
FIG. 5: Delayed Type Hypersensitivity (DTH). Patients were inoculated with 100 μg AE37 peptide without GM-CSF prior (pre) to the initiation of and one month after (post) completion of the six dose vaccine schedule. Local reaction to AE37 was measured (mean diameter of the induration) 48-72 hours later.
Figure 6:
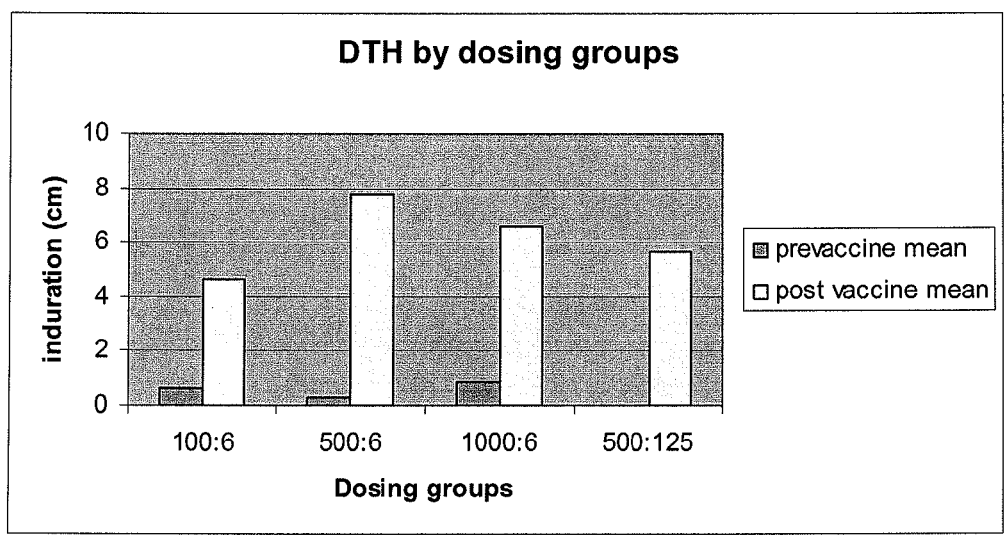
FIG. 6: DTH by dosing groups. The pre- and post-vaccination mean reaction of each dosing group is shown. The x-axis labels describe the dosing regimen. 100:6=100 μg AE37 plus 250 μg GM-CSF, six doses; 500:6=500 μg AE37 plus 250 μg GM-CSF initially, six doses; 1000:6=initially 1000 μg AE37 without GM-CSF, six doses; 500:125=500 μg AE37 plus 125 μg GM-CSF, six doses.
Figure 7:
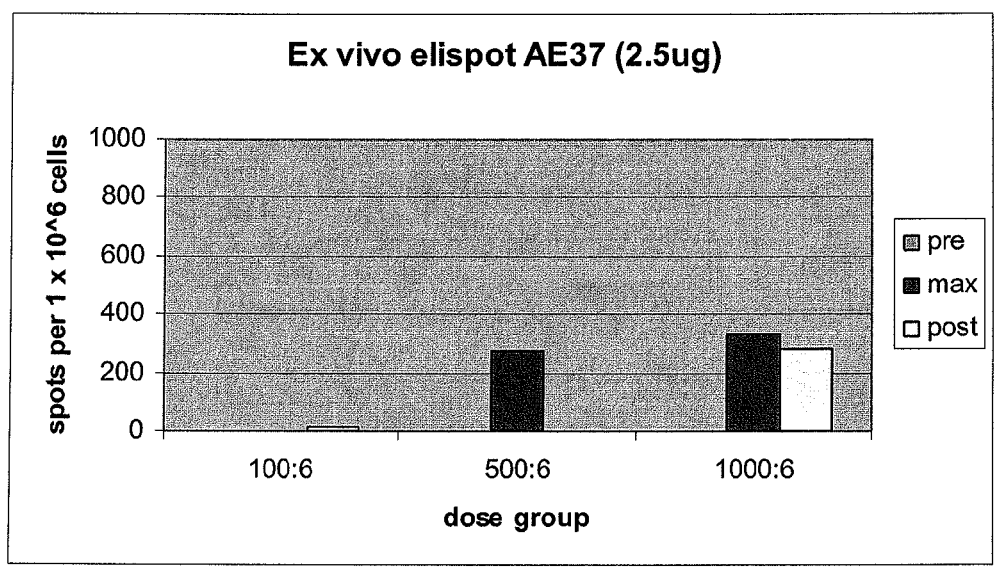
FIGS. 7-10: Ex Vivo Interferon-γElispot. PBMC's were drawn from patients before (pre) the first inoculation, before each subsequent monthly inoculation, and one month after the series ended (post). PBMC's were stimulated with peptide and IFN-γ activity was measured. The diagram represents the number of spots per million PBMC's before, during, and after the vaccination series. "Max" is the highest of the six measurements taken before each inoculation in the series.
Figure 8:
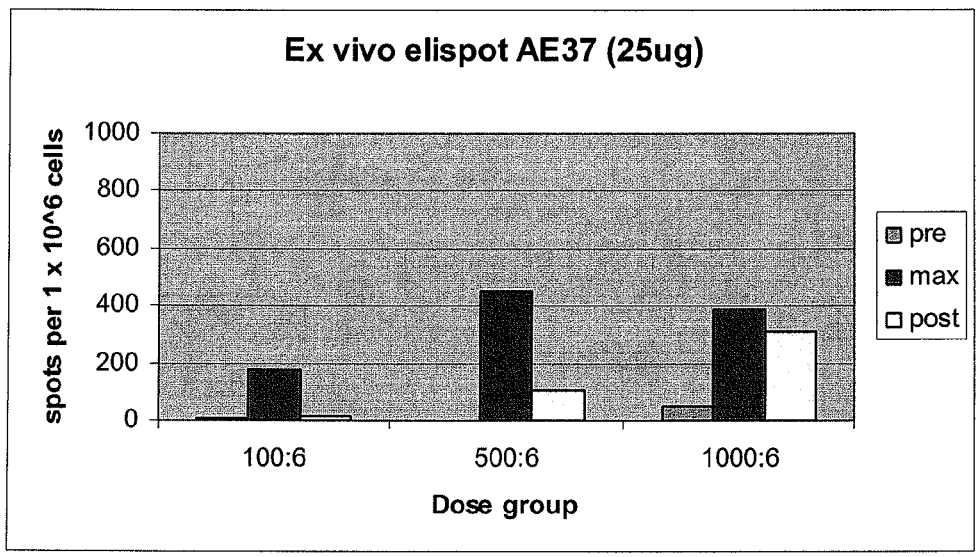
Figure 9:
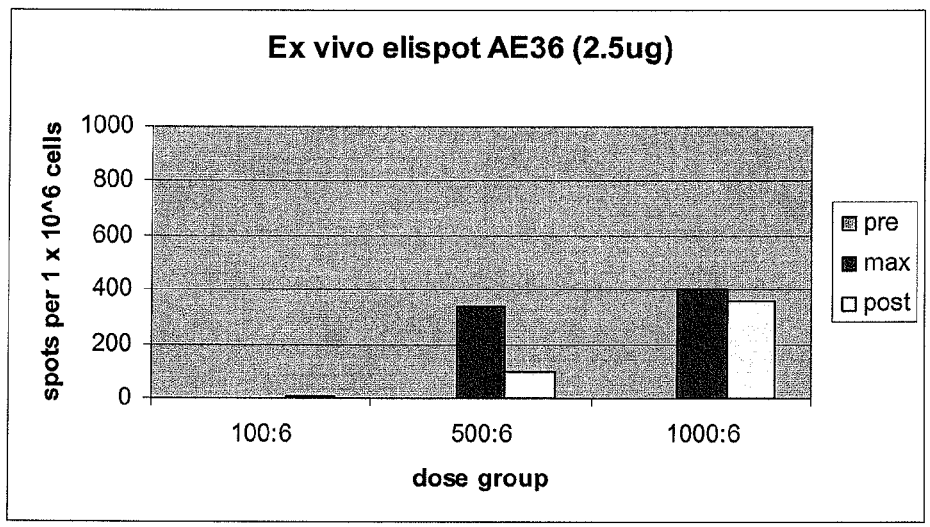
Figure 10:
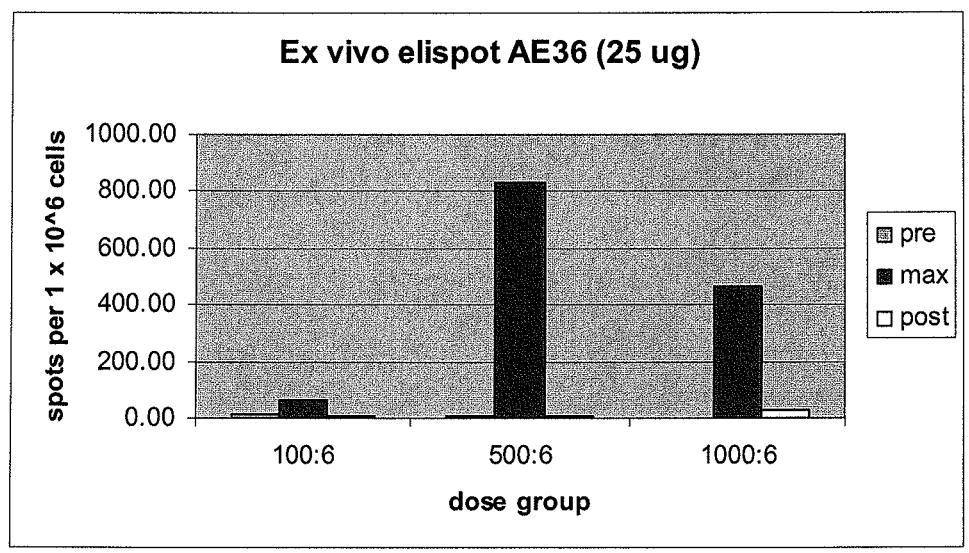
Figure 11:
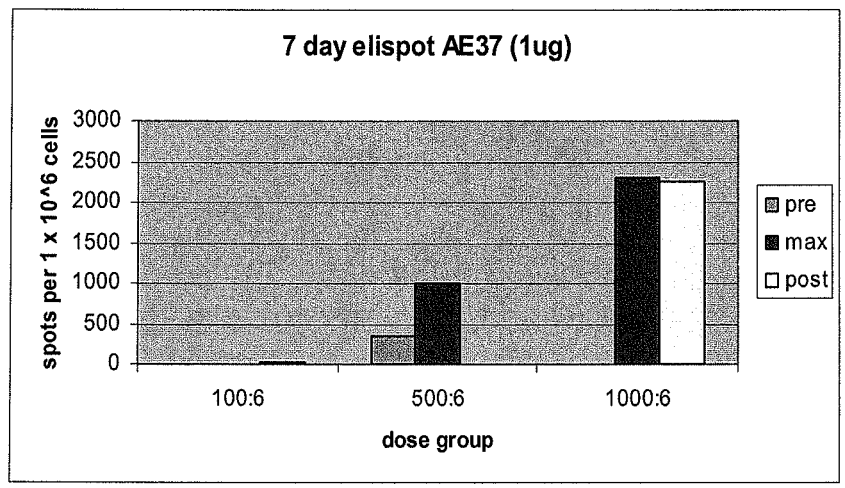
FIGS. 11-14: 7 Day Elispot. PBMC's were drawn from patients before (pre) the first inoculation, before each subsequent monthly inoculation, and one month after the series ended (post). PBMC's were stimulated and allowed to incubate with peptide for seven days before CTL-ImmunoSpot Analysis. The diagram represents the number of spots per million PBMC's before, during, and after the vaccination series. "Max" is the highest of the six measurements taken before each inoculation in the series.
Figure 12:
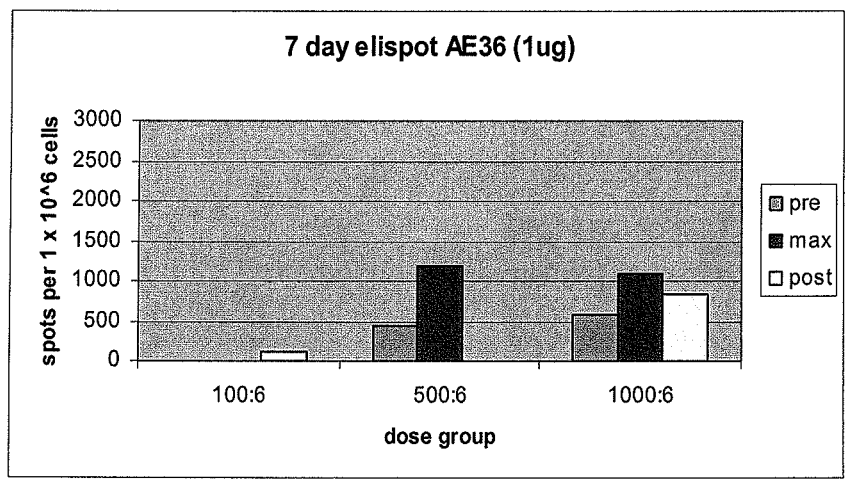
Figure 13:
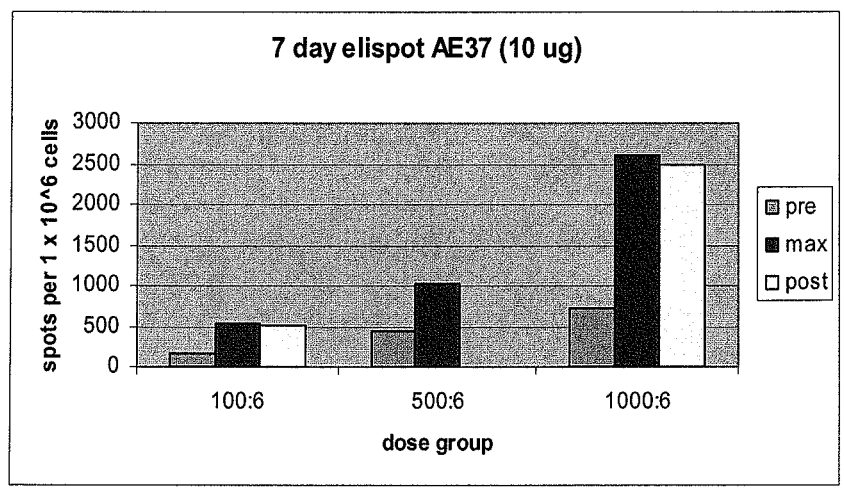
Figure 14:
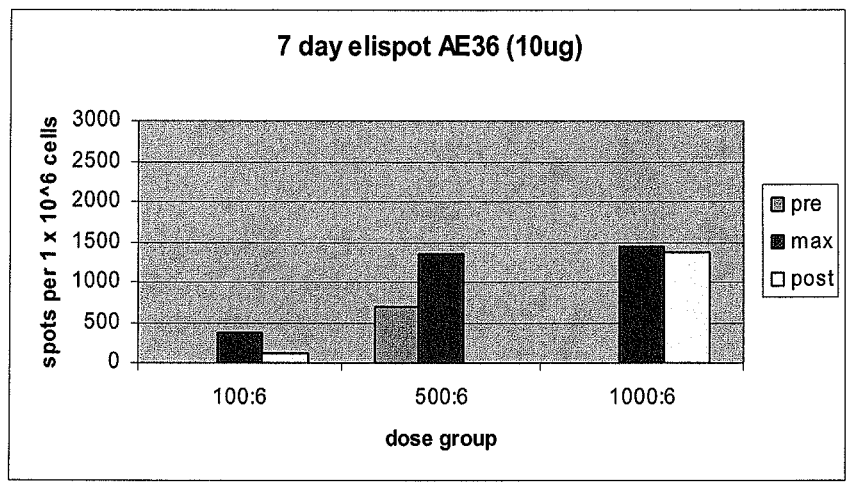
Figure 15:
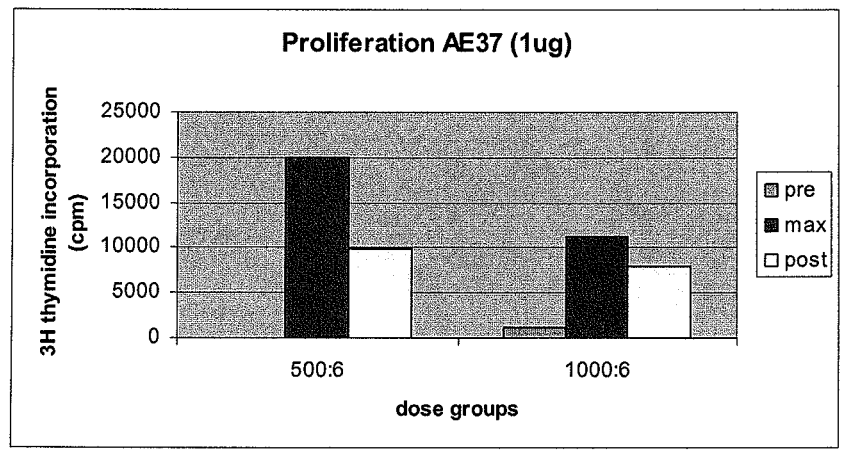
FIGS. 15-18: Proliferation of T cells. PBMC's were drawn from patients before (pre) the first inoculation, before each subsequent monthly inoculation, one month after the series ended (post), and six months after the series ended (memory). PBMC's stimulated and incubated with peptide were pulsed with radioactive $^3$H-thymidine and counted with a scintillation counter. The amount of $^3$H-thymidine incorporated is associated with the peptide-specific proliferative activity of the cultures.

The mean diameter of local reaction pre vaccine was 4.9 mm (range 0-17 mm) and the mean diameter post-vaccine was 62 mm (range 12-106 mm) ($p<0.0001$) (FIGS. 5-6). DTH did not correlate with other measures of immunologic response.

In Vivo Trials

CD4$^+$ T helper peptides from HER2/neu have been evaluated in vaccine trials. The Ii-Key addition, a 4-amino-acid LRMK modification, increases vaccine potency when compared to unmodified class II epitopes. We present results of a prospective, randomized, single-blinded phase II clinical trial of the Ii-Key hybrid HER2/neu peptide (AE37)+GM-CSF immunoadjuvant vaccine versus GM-CSF alone in the adjuvant setting in disease-free, high risk breast cancer (BCa) patients to prevent recurrence.

Methods: Disease-free, high risk BCa patients who have completed standard adjuvant therapy are enrolled and randomized to receive six monthly inoculations of either 500 mcg of AE37 with 62.5 or 125 mcg of GM-CSF (Peptide group; PG) or 62.5 or 125 mcg of GM-CSF alone (adjuvant group; AG). Toxicity is assessed after each inoculation using National Cancer Institute Common Terminology Criteria for Adverse Events v3.0 (CTCAE). Immunologic response was monitored by measured delayed type hypersensitivity reactions (DTH) and $^3$H-thymidine proliferative assays for both hybrid AE37 (LRMK+HER2/neu:776-790) and AE36 (unmodified HER2/neu:776-790) peptides. Patients are clinically, radiographically, and pathologically monitored for recurrence of BCa.

Results: Thus far, 120 (49 PG, 71 AG) of the planned 200 patients have completed the primary series. The PG and AG have similar demographic/prognostic characteristics (see, Table 4). Toxicity profiles in the PG and AG were almost identical with no grade 4-5 local toxicities and no grade 3-5 systemic toxicities in either arm. Median DTH reaction to AE36 and AE37 significantly increased from baseline at 1 month after completion of the primary series in the PG group (AE36: 0.0±0.8 cm to 15.3±2.1 cm; AE37: 0.0±0.7 cm to 24.5±2.6 cm; p<0.0001) and did not change in the AG group (AE36: 0.0±0.5 cm to 0.0±1.4 cm; AE37: 0.0±0.7 cm to 0.0±1.6 cm; p>0.05). Median proliferation response to AE36 and AE37 significantly increased from baseline at 3, 6, and 12 months after the start of the vaccine series in the PG (p<0.015) and did not significantly change in the AG. At a median follow up of 13 months, there have been no (0.0%) recurrences in the PG (0/49) compared to 7.0% (5/71) in the AG (p=0.08).

TABLE 4

| Demographics | | | |
|---|---|---|---|
| | Peptide | Adjuvant | p = |
| N = | 49 | 71 | |
| Age (median) | 49 | 52 | 0.06 |
| Node Positive | 75.5% | 62.1% | 0.16 |
| Grade 3 | 48.9% | 57.8% | 0.44 |
| Tumor >= 2 cm | 55.1% | 56.1% | 1 |

TABLE 4-continued

| Demographics | | | |
|---|---|---|---|
| | Peptide | Adjuvant | p = |
| ER/PR neg | 38.8% | 40.9% | 0.84 |
| HER2 overexpress | 59.2% | 60.6% | 1 |

The modified peptide AE37 is safe with the observed toxicities primarily due to the GM-CSF immunoadjuvant. AE37 elicits a strong HER2/neu-specific in-vivo and ex-vivo immune response to the modified and unmodified peptides. Importantly, the AE37 peptide vaccine protects against BCa recurrences.

CONCLUSIONS

AE37 appears to be safe and well-tolerated with minimal systemic toxicity observed. The AE37 peptide vaccine protects against BCa recurrences. Robust local reactions lead to dose reduction and eventual elimination of the immunoadjuvant GM-CSF. Despite no immunoadjuvant, in vitro and in vivo immunologic responses were significant to both AE37 and the native AE36. To our knowledge, this is the first report of a peptide vaccine derived from a tumor-associated antigen being successful in eliciting an immunologic response in cancer patients without an immunoadjuvant. To our knowledge, this is also the first report of a peptide vaccine derived from a tumor-associated antigen being successful in protecting against BCa recurrences.

What is claimed is:

1. A method of preventing or reducing recurrence of a cancer in a disease-free breast cancer patient, the cancer being characterized by expression of Her-2/neu, comprising:
   a) providing an Ii-Key/MHC class II hybrid construct in a pharmaceutically acceptable carrier, the construct consisting of:
      i) the LRMK (SEQ ID NO: 2) amino acid residues of Ii protein; and
      ii) an MHC class II epitope-containing segment of Her-2/neu consisting of the sequence GVGSPYVSR-LLGICL (SEQ ID NO.: 3) linked at its N-terminus to the residues of element a)i); and
   b) stimulating a disease-free breast cancer patient's immune system by vaccination with the hybrid construct of step a) under conditions appropriate for the stimulation of an immune response.

2. The method of claim 1 wherein the immune response comprises an increase in CD4+ T cell production.

3. The method of claim 1 wherein the immune response comprises an increase in a CD4+ T cell response specific to native Her-2/neu peptide.

* * * * *